(12) United States Patent
Sa et al.

(10) Patent No.: US 11,703,373 B2
(45) Date of Patent: Jul. 18, 2023

(54) PATIENT WEIGHT ESTIMATION FROM SURFACE DATA USING A PATIENT MODEL

(71) Applicant: Siemens Healthcare GmbH, Erlangen (DE)

(72) Inventors: Ruhan Sa, Amherst, NY (US); Birgi Tamersoy, Erlangen (DE); Yao-jen Chang, Princeton, NJ (US); Klaus J. Kirchberg, Plainsboro, NJ (US); Vivek Kumar Singh, Princeton, NJ (US); Terrence Chen, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 927 days.

(21) Appl. No.: 16/283,864

(22) Filed: Feb. 25, 2019

(65) Prior Publication Data
US 2020/0271507 A1 Aug. 27, 2020

(51) Int. Cl.
*G01G 9/00* (2006.01)
*A61B 5/107* (2006.01)
(Continued)

(52) U.S. Cl.
CPC ........... *G01G 9/005* (2013.01); *A61B 5/0064* (2013.01); *A61B 5/0077* (2013.01); *A61B 5/0082* (2013.01); *A61B 5/107* (2013.01); *A61B 5/1073* (2013.01); *A61B 5/1079* (2013.01); *A61B 5/4839* (2013.01); *A61B 5/7264* (2013.01); *A61B 5/7267* (2013.01); *A61B 5/7271* (2013.01); *A61B 5/7278* (2013.01); *A61B 6/542* (2013.01); *A61B 6/544* (2013.01);
(Continued)

(58) Field of Classification Search
CPC ........ A61B 2560/0475; A61B 2576/00; A61B 5/0064; A61B 5/0077; A61B 5/0082; A61B 5/107; A61B 5/1073; A61B 5/1077; A61B 5/1079; A61B 5/4839; A61B 5/7203; A61B 5/7264; A61B 5/7267; A61B 5/7271; A61B 5/7278; A61B 6/542; A61B 6/544; G01G 19/44; G01G 9/005; A61N 2005/1059; A61N 5/103; A61N 5/1031; A61N 5/1039; G16H 50/20
See application file for complete search history.

(56) References Cited

U.S. PATENT DOCUMENTS 9,524,582 B2 12/2016 Ma
11,257,259 B2 * 2/2022 Teixeira ............... A61B 5/0033
(Continued)

FOREIGN PATENT DOCUMENTS

CN 103983334 A 8/2014
CN 106504283 A 3/2017
(Continued)

OTHER PUBLICATIONS

Clarivate Analytics English translation of CN 106529399, accessed Dec. 31, 2021.*
(Continued)

*Primary Examiner* — Amelie R Davis

(57) ABSTRACT

For patient weight estimation in a medical imaging system, a patient model, such as a mesh, is fit to a depth image. One or more feature values are extracted from the fit patient model, reducing the noise and clutter in the values. The weight estimation is regressed from the extracted features.

10 Claims, 4 Drawing Sheets

(51) Int. Cl.
A61B 6/00 (2006.01)
A61B 5/00 (2006.01)
A61N 5/10 (2006.01)
G01G 19/44 (2006.01)

(52) U.S. Cl.
CPC ............ *A61N 5/103* (2013.01); *A61N 5/1031* (2013.01); *A61N 5/1039* (2013.01); *G01G 19/44* (2013.01); *A61B 2560/0475* (2013.01); *A61B 2576/00* (2013.01); *A61N 2005/1059* (2013.01)

(56) References Cited

U.S. PATENT DOCUMENTS

| | | | |
|---|---|---|---|
| 11,284,850 B2* | 3/2022 | Singh | A61B 6/545 |
| 2002/0028003 A1 | 3/2002 | Krebs et al. | |
| 2016/0253798 A1* | 9/2016 | Barrett | G06V 10/82 348/77 |
| 2016/0262714 A1* | 9/2016 | Krauss | A61B 6/544 |
| 2016/0306924 A1* | 10/2016 | Singh | G16H 30/20 |
| 2018/0218351 A1 | 8/2018 | Chaubard et al. | |
| 2019/0357844 A1* | 11/2019 | Raupach | A61B 5/4872 |

FOREIGN PATENT DOCUMENTS

| | | | |
|---|---|---|---|
| CN | 106529006 A | | 3/2017 |
| CN | 106529399 A | | 3/2017 |
| CN | 107334486 A | | 11/2017 |
| CN | 109059798 | * | 2/2021 ............ G01G 19/50 |
| EP | 3571997 A1 | | 3/2002 |
| KR | 20160110070 A | | 9/2016 |
| WO | 2016139203 A1 | | 9/2016 |

OTHER PUBLICATIONS

Clarivate Analytics English translation of CN 103983334, accessed Dec. 31, 2021.*
Dialog Foreign Patent Finder machine translation of CN 106529399 with paragraph numbers, accessed Jul. 18, 2022.*
Clarivate Analytics English Translation of CN 109059798, accessed Jul. 18, 2022.*
Pfitzner et al. "Body Weight Estimation for Dose-Finding and Health Monitoring of Lying, Standing and Walking Patients Based on RGB-D Data." Sensors (Basel). May 2018; 18(5): 1311.*
Anguelov, Dragomir, et al. "SCAPE: shape completion and animation of people." ACM transactions on graphics (TOG) vol. 24. No. 3. ACM, 2005.
Caesar "The Most Comprehensive Source for Body Measurement Data" http://store.sae.org/caesar/ Accessed Feb. 20, 2019.
Coe, T. R., et al. "The accuracy of visual estimation of weight and height in pre-operative supine patients." Anaesthesia 54.6 (1999): 582-586.
Diedler, Jennifer, et al. "Is the maximum dose of 90 mg alteplase sufficient for patients with ischemic stroke weighing 100 kg?." Stroke 42.6 (2011): 1615-1620.
Fernandes, C. M., et al. "How accurately do we estimate patients' weight in emergency departments?." Canadian Family Physician 45 (1999): 2373-2376.
Pfitzner, Christian, et al. "Body Weight Estimation for Dose-Finding and Health Monitoring of Lying, Standing and Walking Patients Based on RGB-D Data." Sensors (Basel, Switzerland) 18.5 (2018).
Prakash, Priyanka, et al. "Is weight-based adjustment of automatic exposure control necessary for the reduction of chest CT radiation dose?." Korean journal of radiology 11.1 (2010): 46-53.
Singh, Vivek, et al. "Darwin: Deformable patient avatar representation with deep image network." International Conference on Medical Image Computing and Computer-Assisted Intervention. Springer, Cham, 2017.
Velardo, Carmelo, and Jean-Luc Dugelay. "Weight estimation from visual body appearance." Biometrics: Theory Applications and Systems (BTAS), 2010 Fourth IEEE International Conference on. IEEE, 2010.
Velardo, Carmelo, and Jean-Luc Dugelay. "What can computer vision tell you about your weight?." Signal Processing Conference (EUSIPCO), 2012 Proceedings of the 20th European. IEEE, 2012.
Mienon, Shyaman, Kelly: "How accurate is weight estimation in the emergency department?", Emergency Medicine Australasia, vol. 17.2, 2005, pp. 113-116.

* cited by examiner

PATIENT WEIGHT ESTIMATION FROM SURFACE DATA USING A PATIENT MODEL

BACKGROUND

The present embodiments relate to patient weight estimation for dosing the patient. Body weight is important information when adjusting drug dosage or radiation dosage in a clinical setting. For example, without a weight-based adjustment, patients are exposed to a 17-43% higher radiation-dose from a chest computed tomography (CT) scan.

Accurate weight information is not always available. In one study for emergency stroke treatment, 14.6% of the patients are weighed with the weights for the rest of the patients being visually guessed by physicians or nursing staff. Health care workers have only moderate accuracy in estimating weight of the patients. The lack of accurate weight information is due to several complex reasons. For instance, it is not possible to use common standing scale method for patients with severe conditions, such as trauma or stroke. Moreover, the time requirement for emergency treatment may not allow weighing.

Anthropometric measurements may be used to estimate human body weight. In one approach, anthropometric features are manually measured from an image to learn a correlation of features and body weight through regression. In a more automated approach, features are extracted directly from a depth image. Directly extracting features from the depth image may be problematic when the scene is cluttered and noisy.

SUMMARY

Systems, methods, and instructions on computer readable media are provided for patient weight estimation in a medical imaging system. A patient model, such as a mesh, is fit to a depth image. One or more feature values are extracted from the fit patient model, reducing the noise and clutter in the values. The weight estimation is regressed from the extracted features.

In a first aspect, a method is provided for patient weight estimation from surface data in a medical imaging system. The surface data is data representing a surface or outside of the patient, such as by capturing an outer surface of a patient with a sensor. A patient model is fit to the surface data. The patient model is a mesh, statistical shape model, or other generic parameterization of an outer surface. The fit deforms the patient model to fit to the surface data of the particular patient. A value for each of one or more features are extracted from the patient model as fit. The features are shape features or other characterization of the patient model. A weight of the patient is estimated by input of the value or values for the one or more features to a machine-learned regressor. The patient is dosed based on the weight.

The sensor may be a depth sensor or a camera where the surface data is based on optical measurements. The patient model may be fit as a statistical shape model to the surface data. The dosing may apply radiation to the patient where the amount (e.g., frequency, amplitude level, number of applications, or other dosing level) is based on the weight.

In one embodiment, the shape feature is a body volume indicated by the fit patient model. In other embodiments, one or more features are used for each of different body parts. The weight is estimated for the different body parts, such as estimating part weights for the different body parts and summing the part weights. In another embodiment, the values extracted from the fit patient model are shape manifold coefficients. The coefficients are parameterizations of the shape, such as through a mathematical manifold based on a fit mesh.

The estimation uses any learned regression, such as a machine-learned regressor being a fully convolutional network. A machine-learned or other linear regressor may be used.

In a second aspect, a medical imaging system is provided for patient weight estimation. A depth sensor is configured to measure depths to a patient. An image processor is configured to form a mesh for the patient using the depths and regress a weight of the patient from the mesh as formed for the patient. The weight may be regressed with a machine-learned regressor. A memory is configured to store the regressed weight, such as storing for use in determining or controlling dosage.

In one embodiment, the depth sensor is a depth camera. After fitting the mesh, the image processor is configured to regress in response to input to a machine-learned regressor. A therapeutic radiation scanner is configured to apply a radiation dose to the patient where an amount of the radiation dose is based on the weight.

The image processor may be configured to extract a value for a shape feature from the mesh as formed for the patient and to regress the weight from the value. The shape feature may be a volume for an entirety of the mesh or for a part of the mesh. The image processor may be configured to extract values for a shape manifold from the mesh as formed for the patient and to regress the weight from the values.

In a third aspect, a method is provided for patient weight estimation in a medical imaging system. A sensor captures an outer surface of a patient. A shape feature value is extracted from a patient model fit to the outer surface captured with the sensor. A body weight of the patient is estimated through regression from the shape feature value.

In one embodiment, a machine-learned regressor estimates. The patient is dosed where an amount of a dose is based on the estimated body weight.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

Patient weight is estimated from a depth image using a patient three-dimensional (3D) model. To overcome the challenges caused by noise or clutter, a regression-based weight estimation from the depth image of the patient uses the patient 3D surface model. Instead of capturing shape information directly from cluttered depth image of the scene, using the fitted patient model as the middle layer to represent the patient body provides for more robust weight estimation. A weight estimation regression is based on input depth image and fitted patient model. Various reliable human shape features, for example, shape volume, shape manifold etc., may be extracted from the fit model. The extracted features may then be used to estimate patient body weight through a regression method. The correlation of patient weight and captured image is formulated as correlation between patient weight and shape features extracted from fitted patient model.

In one embodiment, a depth image is input to the weight estimation framework. A patient model represented by human surface mesh is then extracted from the input. The human surface mesh is acquired through fitting a template human surface mesh onto the current patient input. The fitted patient model captures an accurate estimate of the patient shape, from which various related body measurements may be extracted to estimate human body weight.

Since the depth image captured from a real-world setting is usually noisy, directly extracting patient body features from the depth image is error prone. Instead, a fitted patient model captures the shape information of the patient for weight estimation without being affected by the noise coming from the surrounding objects. The correlation of the extracted shape features and the patient weight is learned through regression methods to robustly estimate patient body weight.

Robust weight estimation may be used in many clinical applications. For instance, while the patient is on a medical scanner (e.g., diagnostic imager and/or therapeutic scanner), the accurate weight is estimated based on a depth sensor image. The weight may be estimated regardless of the severity of the patient's condition. The estimated weight may then assist the decision-making process for dosage control, which is an important factor to both the quality of the scan and the patient's health.

In one embodiment, the shape features are coefficients of a shape manifold. More complicated features may be used, such as features for body part information, from which different body part shape information is used to estimate weight more robustly. The framework may also be extended for other applications, such as estimating patient height or other characteristics.

Figure 1:
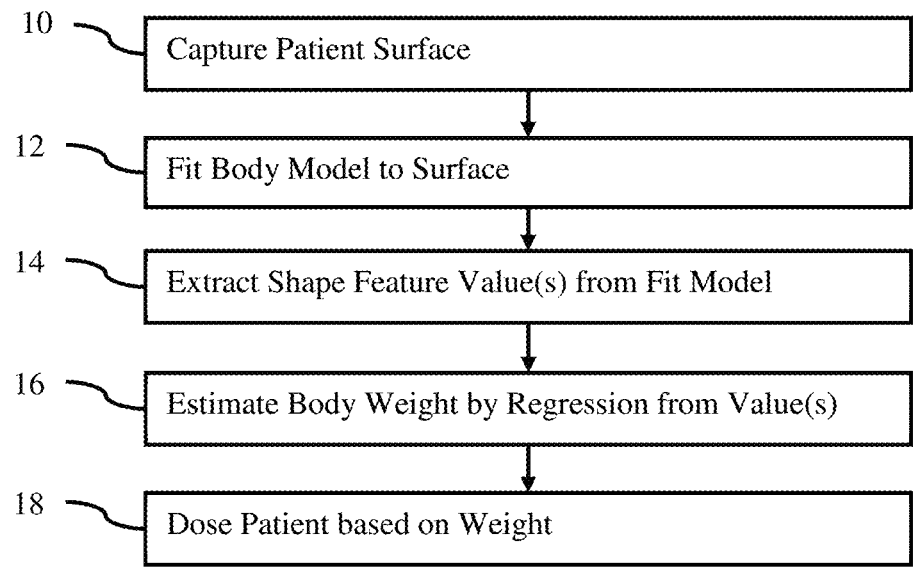
FIG. 1 is a flow chart diagram of one embodiment of a method for patient weight estimation from surface data in a medical imaging system.

FIG. 1 is a flow chart diagram of one embodiment of a method for patient weight estimation in a medical imaging system. The weight estimation is from imaging an outer surface of the patient. An imaging sensor is used in the medical imaging system to acquire surface data (e.g., external surface) of the patient.

Figure 2:
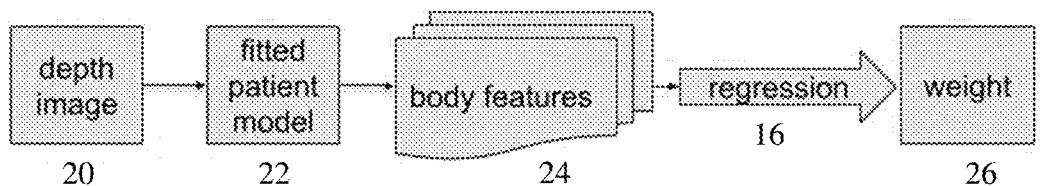
FIG. 2 illustrates example workflow for weight estimation using a fitted patient model.

FIG. 2 shows an example representation of the method of FIG. 1. The method takes a depth image 20 as input and fits (personalizes) a patient surface model 22 based on the depth image. The personalized patient surface model 22 is then used to extract various features 24, which are used to estimate 16 the weight 26 through regression. Based on fitting the surface model 22 to the data from the sensor, the weight is estimated from a characteristic of the fit surface model 22.

The method of FIG. 1 is performed by the medical imaging system. The sensor, such as a depth camera, captures the patient surface. An image processor fits the model, extracts the shape feature values, and estimates the body weight of the patient. The image processor, a physician, and/or a scanner (e.g., x-ray device) set the dose based on the weight. Other devices may be used to perform any of the acts.

The method is performed in the order shown (e.g., top to bottom or numerical), but other orders may be used. Additional, different or fewer acts may be provided. For example, act 18 is not provided.

In act 10, a sensor captures an outer surface of a patient. The sensor is a depth sensor, such as a 2.5D or RGBD sensor (e.g., Microsoft Kinect 2 or ASUS Xtion Pro). The depth sensor may directly measure depths, such as using time-of-flight, interferometry, or coded aperture. The depth sensor may be a camera or cameras capturing a grid projected onto the patient. The sensor may be multiple cameras capturing 2D images from different directions, allowing reconstruction of the outer surface from multiple images without transmission of structured light. Other optical or non-ionizing sensors may be used.

The sensor is directed at a patient. The sensor captures the outer surface of the patient from one or more perspectives. Any portion of the outer surface may be captured, such as the entire patient viewed from one side from head to toe and hand to hand or just the torso. The sensor captures the outer surface with the patient in a particular position, such as capturing a front facing surface as the patient lies in a bed or on a table for treatment or imaging.

The outer surface is the skin of the patient. In other embodiments, the outer surface includes clothing. The sensor may use a frequency that passes through clothing and detects skin surface. Alternatively, the outer surface is the clothing and the fitting of the patient model accounts for the clothing.

Figure 3:
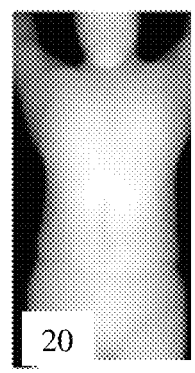
FIG. 3 is an example depth image.

The outer surface is captured as depths from the sensor to different locations on the patient, an image or photograph of the outside of the patient, or both. The sensor outputs the sensed image and/or depths. The measurements of the outer surface from the sensor are surface data for the patient. FIG. 3 shows an example image 20 from surface data where the intensity in grayscale is mapped to the sensed depth. Alternatively, the sensor measurements are processed to determine the outer surface information, such as stereoscopically determining the outer surface from camera images from different angles with image processing.

In one embodiment, the surface data may include different representations of the patient. Two or more channels are created. For example, two images have pixel intensity modulated by the amplitude of the information for the channel (e.g., one by depth and the other by color). In one embodiment, given a 3D surface of the patient's body (skin surface), 2D projections of this data—skin surface image (e.g., height of the surface from the scanner table at each location in the image) and depth image (e.g., measure the thickness of the person at each location in the image)—are formed by image processing from the output of the sensor. Each channel provides different information. One channel provides a distance or height of front surface locations to a bed or table on which the patient lies, to the sensor, and/or relative to another location. The outer surface as sensed and the known location of the sensor to the bed are used to determine the distance. Another channel is a thickness of the patient. The thickness may be a difference of a given depth from the maximum and minimum depth. Other thickness may be used. The first channel stores the depth of the body surface as observed from the front or looking at the patient resting on the patient bed, and second channel stores the thickness computed by measuring the distance between the closest and furthest point as observed from the front. Other channels may be used, such as one channel for depth from the sensor and another channel for optical image of the patient. Other surface data may be used.

The surface data is used at the resolution of the sensor. For example, the surface data is at 256×256 pixels. Other sizes may be used, including rectangular fields of view. The surface data may be filtered and/or processed. For example, the surface data is altered to a given resolution. As another example, the surface data is down sampled, such as reducing 256×256 to 64×64 pixels. Each pixel may represent any area, such as each pixel as down sampled to 64×64 representing 1 $cm^2$ or greater. Alternatively, the sensor captures at this lower resolution. The surface data may be cropped, such as limiting the field of view. Both cropping and down sampling may be used together, such as to create 64×64 channel data from 256×312 or other input channel data. Greater or lower resolution may assist in regression.

In another approach, the surface data is normalized prior to input. The surface data is rescaled, resized, warped, or shifted (e.g., interpolation). The surface data may be filtered, such as low pass filtered.

In act 12, the image processor fits a patient model to the surface data. The patient model is a generic representation of surface of a human or part of a human. Different models may be used for different body types, such as a male or female model. The patient model is not specific to the patient. For example, the patient model is a statistical shape model. The patient model is not specific to any other patient or is specific to a patient meeting a norm.

Any representation may be used for the model. In one embodiment, the model is formed from a mesh, such as a mesh of triangles. Other meshes may be used. Other representations of a 3D surface may be used.

The image processor fits the patient model to the surface data for the patient to be treated or imaged. The fit transforms or distorts the patient model based on the sensed outer surface of the patient. The generic patient model is personalized to the outer surface of the patient by fitting to the surface data. The fit may be an iterative optimization, such as testing different alterations of the model where the alteration is controlled based on a closeness of fit or difference between the model and the surface data.

Any now known or later developed fit of a body surface model to captured surface data for a patient may be used. For example, a SCAPE model is fit to the surface data based on minimization of differences. In one embodiment, the depth camera image 20 of a subject is converted to a 3D point cloud. A plurality of anatomical landmarks is detected in the 3D point cloud. A 3D avatar mesh is initialized by aligning a template mesh to the 3D point cloud based on the detected anatomical landmarks. A personalized 3D avatar mesh of the subject is generated by optimizing the 3D avatar mesh using a trained parametric deformable model (PDM). The optimization is subject to constraints that take into account clothing worn by the subject and the presence of a table on which the subject in lying.

In another embodiment, a statistical shape model is fit to the depths as the surface data. The statistical shape model is a mesh or other representation of an average or other statistical representation of an outside of a human or part of a human. The statistical shape model includes probabilities or other constraints on alteration, so that the fitting maintains the shape based on statistics.

In yet another embodiment, a personalized 3D mesh of a person is generated by a model-based approach to fit a human skeleton model to depth image data of the person. The estimated pose skeleton is then used to initialize a detailed parametrized deformable mesh (PDM) that was learned in an offline training phase. The PDM is then optimized to fit the input depth data by perturbing the body pose and shape. A sampling-based optimization procedure fits the PDM to the depth data. Unlike the shape completion and animation of people (SCAPE) model, which is only applied to data with a skin clad subject, the sampling-based approach deals with clothing variations of the subject. Furthermore, the sampling-based approach also enables embodiments to deal with bias introduced due to sensor noise.

Figure 4:
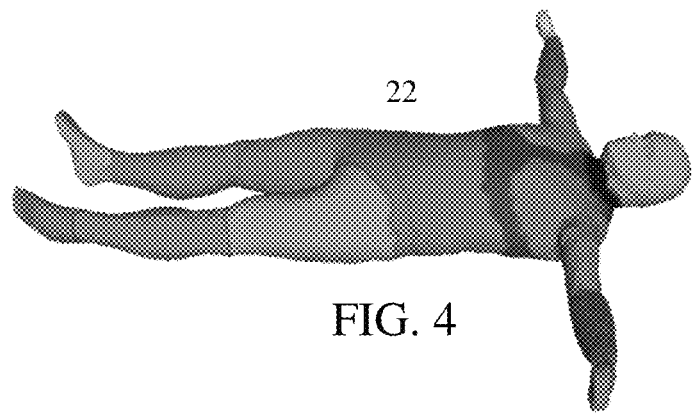
FIG. 4 shows an example fit patient model.

FIG. 4 shows an example fit patient model 22. A body surface mesh indicates the body shape. Based on this fitted body surface mesh, value(s) for feature(s) used to estimate body weight may be extracted.

In act 14, the image processor extracts a value for each of one or more features from the patient model as fit to the surface data for the patient. A shape feature value is extracted from the patient model fitted to the outer surface captured with the sensor.

The extraction is by calculation, measurement, and/or image processing. The image processor uses the model as fit to extract values less susceptible to noise and clutter than if extracted from the depths or other sensor measurements.

Any feature or features may be used. The features are shape features, such as parameters that characterize the shape of the outer surface of the patient as represented by the fit patient model. Example shape features may include volume, area, diameter, circumference, length, width, curvature, other anthropometric measure, and/or other geometric measure.

Figure 5:
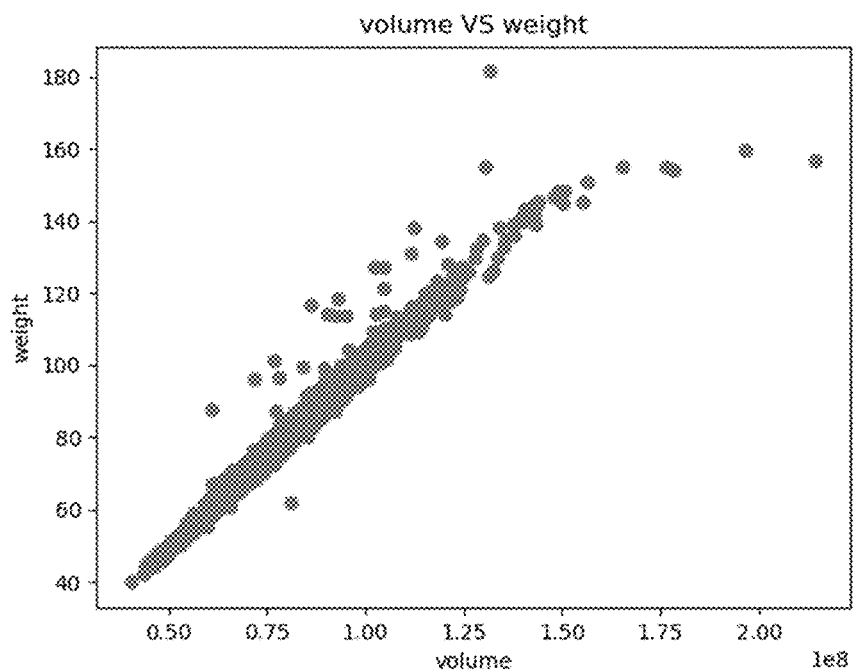
FIG. 5 is a graph showing correlation between weight and volume.

In one embodiment, a value for body volume is extracted. Body volume is one of the indicators of human body weight. FIG. 5 shows a plot the volume information and the corresponding weight from 196 human samples from a public dataset, CAESER. A linear correlation exists between the volume feature and weight.

The volume of the fitted body mesh is calculated and then used to estimate weight information through learned regression. The patient model 22 as fit encloses a volume. The volume here is the volume of the fitted mesh, which is different from patient body volume. If the patient model 22 does not include a part or parts of the patient (e.g., feet, hands, arms, head, and/or legs), the body volume may be of the part included within the patient model 22. The fit model may accurately represent the volume of the patient.

In another embodiment, values are extracted for each of a plurality of different body parts. Values for the same or different feature or set of features are extracted for the different body parts. For a human, different body parts may have different densities. For instance, legs and arms are usually denser than the upper main body (torso), which includes various organs. Having different volumes in different body parts may have an impact on the weight. Based on this observation, values are extracted separately for each individual body part from the fitted body mesh. For example, the volumes of the legs, arms, torso, and head are extracted.

In the fitted body mesh of FIG. 4, different portions of the mesh are labeled for different parts. The different gray scale levels in FIG. 4 show the different parts. The patient model 22, as fit, may include additional, different, or fewer body parts. Values of features, such as volume and/or individual shape coefficients, are extracted for each of the parts.

In yet another embodiment, the image processor extracts values for shape manifold coefficients as the features. Instead of a straightforward shape feature, such as volume, shape manifold information is used. For example, using SCAPE or other fit patient model 22, fitted shape coefficient information of the fitted mesh is extracted. Any parameterization or mathematical representation of the shape may be used. For example, assume $V=\{v_1, v_2, v_3, \ldots, v_n\}$ where V is a shape manifold vector with n dimension. The extracted coefficient vector with n dimension. $v_i$, $i \in [1, n]$, denotes the $i^{th}$ element of the coefficient. Any shape manifold may be used.

In act 16 of FIG. 1, the image processor estimates a body weight of the patient through regression from the shape feature value or values. In one embodiment, a look-up table incorporating the correlation between the shape feature or features and the weight is used. In another embodiment, a function, such as a fit line, is used to determine the weight from an input value of the feature. For example, the volume of the fitted body mesh is used to estimate weight through learned regression. Any regression from various past examples or samples may be used, such as linear regression, least squares, another parametric regression, and/or a non-parametric regression.

In one embodiment, the image processor estimates the weight by input of the value or values for the feature or features into a machine-learned regressor. The machine-learned regressor is any machine learned classifier outputting a continuous variable, such as including a machine-learned linear regression. For example, a neural network is used to regress the relationship between the input features and the output weight. A fully connected neural network or another neural network may be used. A support vector machine, clustering based machine learning, Bayesian, or other machine-learned regressor may be used.

For training the machine-learned network, the machine learning network arrangement is defined. The definition is by configuration or programming of the learning. The number of layers or units, type of learning, and other characteristics of the network are controlled by the programmer or user. In other embodiments, one or more aspects (e.g., number of nodes, number of layers or units, or type of learning) are defined and selected by the machine during the learning. Training data, including many samples of the value or values for one or more features and the corresponding ground truth (i.e., weight), is used to train. The relationship of the input to the output is machine learned. Once trained, the machine-learned model (machine-learned regressor) may be applied to estimate the weight from value or values of one or more features for a patient.

In one embodiment, the machine-learned regression is a trained fully convolutional network. A mapping function $W=f(V, \theta)$ is learned to estimate the weight, denoted by W. The mapping function is modeled as a fully connected neural network, with parameter $\theta$. Through training, the parameter is learned, such as learning the parameter $\theta$ to estimate the weight W from an input volume as the shape feature.

In another embodiment, different regressors are learned for different body parts. The part weights are estimated for the different body parts and summed to get the body weight of the patient. For example, volume or values of individual shape coefficients are extracted for different body parts. The extracted value or values for each body part are then used as the input to each individual regression function (e.g., modeled as different fully connected neural networks). Denote the collection of mapping function as $F=\{f_1, f_2, f_3, \ldots, f_m\}$, where $f_j, j \in [1, m]$, denote the mapping function of $j^{th}$ body part, and m denotes the total number of body parts. The mapping function is modeled as fully connected neural network with parameter $\theta_j$, i.e., $w_j=f_j(x_j, \theta_j)$, in which $x_j$ denote the extracted weight. Then the entire body weight is calculated with $W=\Sigma w_j$. In alternative embodiments, the values for the features from the different parts are input to one machine-learned regressor, which outputs the total body weight without output or direct regression of individual part weights.

Figure 6:
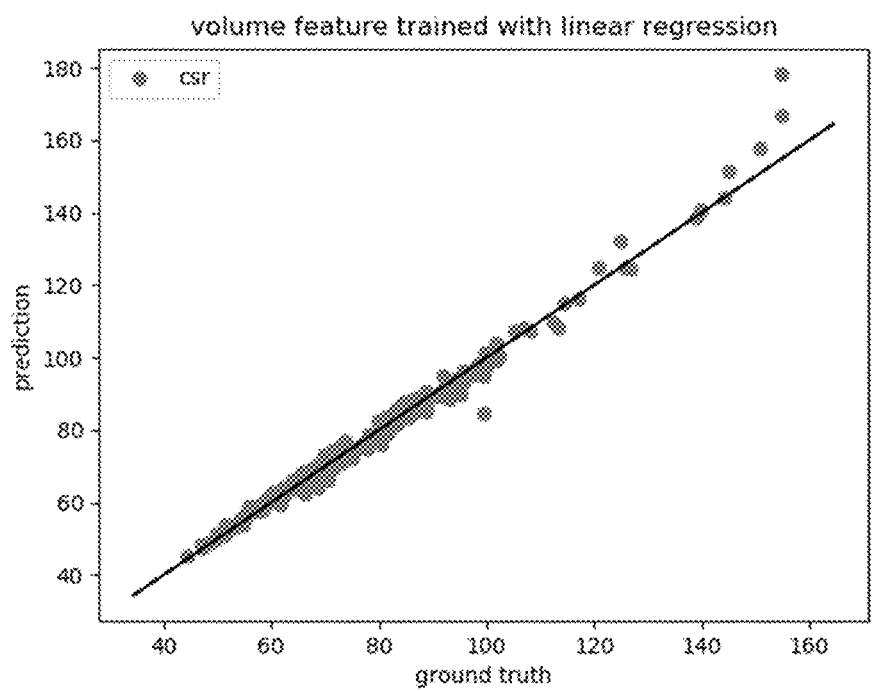
FIG. 6 is a graph showing predicted weight based on volume to actual weight.

FIG. 6 compares estimates of weight from a machine-learned regressor to the actual weights. The machine-learned regressor in the form of a fully connected neural network is trained to estimate weight from volume of the fitted mesh. The volume information is extracted from 1766 fitted body meshes to learn the regression based on this feature to estimate weight. The comparison of FIG. 6 is found from this trained regression on another 196 testing samples. The line y=x is the linear regression where the prediction matches the ground truth exactly. A mean average error of 1.79 kg results. This error may be better than healthcare worker estimation of weight.

In act 18, the patient is dosed based on the weight. A physician determines an amount of a drug dose. The patient ingests the drug, or the drug is injected. The amount of ingested or injected drug is based, at least in part, on the estimated weight.

In another embodiment, the patient is to receive radiation in treatment or diagnostic scanning. An amount of radiation is based on the weight. The amount may be an intensity, duration, frequency, and/or other setting of the x-ray machine controlling how much radiation is applied to the patient and/or a given region of the patient. Patients with less weight receive less radiation. The radiation dose is based on the weight.

In one example, an injured patient is to be treated at a hospital. Due to injury, the patient cannot stand on a scale. Instead, the patient is placed on a bed, such as the table of a therapeutic x-ray system. A depth camera in the room, such as mounted to the therapeutic x-ray system, images the patient. Based on a fitting of a patient model to the surface data from the depth camera, the weight of the patient is estimated. The weight is used to control the dose provided by the therapeutic x-ray system. The weight is used automatically or with manual input to configure the x-ray system to apply a weight-corrected dose particular to the patient.

In another example, the image processor configures a diagnostic medical scanner (e.g., computed tomography, fluoroscopy, or x-ray) based on the weight. The medical scanner may configure itself. The image processor may provide information to a controller of the medical scanner to configure. The image processor may configure by direct control the medical scanner. Alternatively, the user manually configures the medical scanner based on the weight by entry with one or more controls.

One or more settings for imaging or scanning the patient may be adjusted or set using, at least in part, the weight. The weight may assist in planning a medical scan, such as defining a field of view and/or x-ray intensity to control dose from the radiation. For CT scanning, the weight may be used to determine the scan range. This may reduce the amount of ionizing radiation applied to the patient. The weight may assist in scan sequence, coil placement, and/or scan position for magnetic resonance (MR) scanning. For ultrasound scanning, the weight may assist in imaging frequency where a lower frequency is used for heavier patients. For fluoroscopy using dyna-CT scans, the weight may be useful for positioning the patient and/or the scanner and controlling the x-ray source. Any setting or parameter of the medical scanner may be determined or configured based on the weight.

The configured medical scanner scans the patient. The patient is imaged. The imaging is performed based on the configuration of the medical scanner. For therapy, the therapeutic system applies the radiation based on the configuration.

Figure 7:
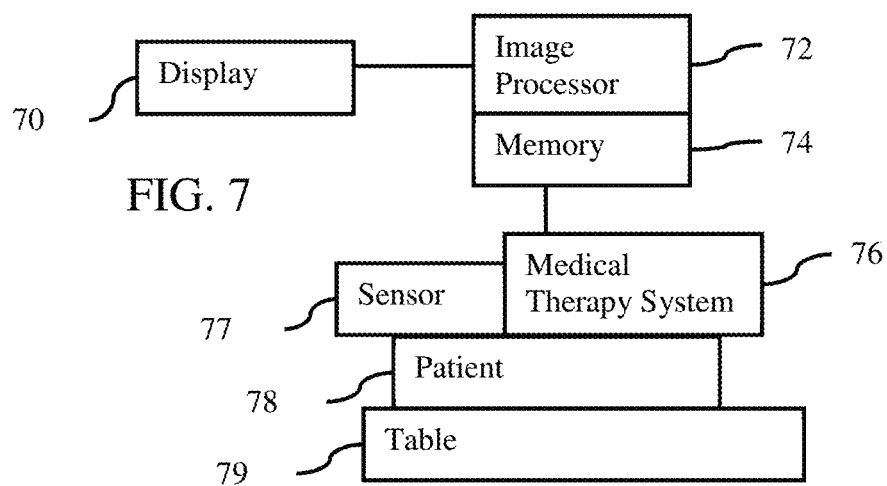
FIG. 7 is a block diagram of one embodiment of a system for patient weight estimation.

FIG. 7 shows one embodiment of a medical imaging system for patient weight estimation. The medical imaging system includes the display 70, memory 74, and image processor 72. The display 70, image processor 72, and memory 74 may be part of the medical therapy system 76, a computer, server, workstation, or other system for image processing medical images from a scan of a patient. A workstation or computer without the medical therapy system 76 may be used as the medical imaging system. The medical imaging system also includes the sensor 77 for sensing (imaging) an outer surface of a patient.

Additional, different, or fewer components may be provided. For example, a computer network is included for remote image generation of locally captured surface data or for local estimation of weight from remotely captured surface data. The machine-learned regressor or other regression is applied as a standalone application on the workstation or a local device or as a service deployed on network (cloud) architecture. As another example, a user input device (e.g., keyboard, buttons, sliders, dials, trackball, mouse, or other device) is provided for user alteration or placement of one or more markers (e.g., landmarks). In yet another example, the medical therapy system 76 is not provided, such as where a drug is to be applied or where a medical diagnostic imager is used instead.

The sensor 77 is a depth sensor or camera. LIDAR, 2.5D, RGBD, stereoscopic optical sensor, or other depth sensor may be used. One sensor 77 is shown, but multiple sensors may be used. A light projector may be provided. The sensor 77 may directly measure depth from the sensor 77 to the patient. The sensor 77 may include a separate processor for determining depth measurements from images, or the image processor 72 determines the depth measurements from images captured by the sensor 77. The depth may be relative to the sensor 77 and/or a bed or table 79.

The sensor 77 is directed to the patient 78. The sensor 77 may be part of or connected to the medical therapy system 76 or is separate from the medical therapy system 76.

The sensor 77 is configured to measure depths to or for a patient. The depths are distances from the sensor 77, table 79, or other location to the patient at various locations on the patient. Any sample pattern over the patient may be used. The sensor 77 outputs depth measurements and/or a surface image.

The image processor 72 is a control processor, general processor, digital signal processor, three-dimensional data processor, graphics processing unit, application specific integrated circuit, field programmable gate array, artificial intelligence processor, digital circuit, analog circuit, combinations thereof, or other now known or later developed device for processing surface data. The image processor 72 is a single device, a plurality of devices, or a network. For more than one device, parallel or sequential division of processing may be used. Different devices making up the image processor 72 may perform different functions, such as fitting a mesh as a patient model by one device and estimating weight by another device. In one embodiment, the image processor 72 is a control processor or other processor of a medical therapy system 76. The image processor 72 operates pursuant to and is configured by stored instructions, hardware, and/or firmware to perform various acts described herein.

The image processor 72 is configured to train a machine learning architecture. Based on a user provided or other source of the network architecture and training data, the image processor 72 learns to relate one or more input variables (e.g., volume and/or other shape feature) to the output variable (e.g., weight and/or height) to train the regressor. The result of the training is a machine-learned regressor or regressors for weight or other prediction.

Alternatively or additionally, the image processor 72 is configured to apply one or more machine-learned regressors. In response to input of a value or values of shape feature or features for a patient, the machine-learned regressor outputs a weight. In other embodiments, the image processor 72 regresses the output without a machine-learned regressor.

The image processor 72 is configured to form a mesh for the patient using the depths from the sensor 77. A mesh is fit to the depths or other output of the sensor as a patient model. The mesh may be fit by detection of the surface of the patient and/or by minimizing differences between a pre-determined mesh shape and the shape represented by the output of the sensor.

The image processor 72 is configured to extract a value for a shape feature from the mesh as formed for the patient. Any shape feature may be used, such as the volume for an entirety of the mesh and/or for a part of the mesh (e.g., arm, leg, head, and torso volumes separately extracted based on boundaries defined by the mesh of the patient model). In one embodiment, the shape features are defined by a shape manifold, so the image processor 72 extracts values for the shape manifold coefficients from the fit mesh.

The image processor 72 is configured to regress the weight from the extracted value or values. The weight of the patient is regressed from the mesh as formed for the patient via values extracted from the fit mesh. Multiple regressors may be used, such as where weights of parts of the patient are regressed and summed.

The display 70 is a CRT, LCD, projector, plasma, printer, tablet, smart phone or other now known or later developed display device for displaying the output, such as an image of or including the weight. The display 70 displays a medical image of the patient and/or of the patient's weight.

The sensor measurements, fit shape model, surface data, network definition, features, machine-learned regressor, extracted values, regressed weight, and/or other information are stored in a non-transitory computer readable memory, such as the memory 74. The memory 74 is an external storage device, RAM, ROM, database, and/or a local memory (e.g., solid state drive or hard drive). The same or different non-transitory computer readable media may be used for the instructions and other data. The memory 74 may be implemented using a database management system (DBMS) and residing on a memory, such as a hard disk, RAM, or removable media. Alternatively, the memory 74 is internal to the processor 72 (e.g. cache).

The instructions for implementing the training or application processes, the methods, and/or the techniques discussed herein are provided on non-transitory computer-readable storage media or memories, such as a cache, buffer, RAM, removable media, hard drive or other computer readable storage media (e.g., the memory 74). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

The medical therapy system 76 is a therapeutic radiation scanner, such as an x-ray or particle therapy system. The medical therapy system 76 operates pursuant to one or more settings to apply radiation to a patient. The settings control the location and radiation dose. The intensity, frequency for a given location, duration of application to a location, and/or other settings are controlled, at least in part, based on the weight. The weight is used to adjust or initially set the amount of radiation dose to be applied. The weight may be used to constrain the amount of dose. Configuration based on the weight may be automatic or manual.

Once configured by the settings, the medical therapy system 76 applies radiation to the patient. The amount of radiation applied is based, at least in part, on the weight. Heavier patients may receive more radiation or less radiation than lighter patients.

In alternative embodiments, a medical scanner is configured to scan an internal region of a patient and generate diagnostic information from the scan. The medical scanner is a CT, MR, PET, SPECT, X-ray, or ultrasound scanner.

The medical scanner is configured to generate diagnostic image information. The configuration uses settings for one or more parameters, such as an X-ray source voltage, table position and/or range of movement, gantry position and/or range of movement, focus, field of view, scan density, detector thresholds, transmission sequence, image processing settings, filtering settings, or image generation settings. Based on the weight generated from the shape features of the model fit to the surface data, one or more settings of the medical scanner are automatically or manually set. The patient 78 is imaged by the medical scanner using the settings.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for patient weight estimation from surface data in a medical imaging system, the method comprising:
   capturing, with a sensor, an outer surface of a patient, the surface data being from the capturing of the outer surface of the patient;
   deforming a generic patient model to fit to the surface data of the patient;
   extracting one or more values for each of a plurality of different body parts of the patient from the deformed generic patient model;
   estimating a weight of each of the plurality of body parts of the patient by input of the one or more values for the plurality of different body parts to a respective machine-learned regressor for each of the plurality of body parts; and
   applying radiation to the patient where an amount of radiation is based on a summed weight of the plurality of body parts.

2. The method of claim 1 wherein capturing comprises capturing with the sensor being a depth sensor.

3. The method of claim 1 wherein capturing comprises capturing with the sensor being a camera where the surface data is based on optical measurements.

4. The method of claim 1 wherein the generic patient model comprises a statistical shape model.

5. The method of claim 1 wherein extracting comprises extracting a value of a shape feature for each of the plurality of body parts.

6. The method of claim 5 wherein extracting the value of the shape feature comprises extracting a volume of each of the plurality of body parts from the deformed generic patient model.

7. The method of claim 1 wherein estimating comprises estimating with the machine-learned regressor comprising a fully convolutional network.

8. The method of claim 1 wherein estimating comprises estimating with the machine-learned regressor comprising a machine-learned linear regressor.

9. A method for patient weight estimation in a medical imaging system, the method comprising:
   capturing, with a sensor, an outer surface of a patient;
   deforming a generic patient model to fit the outer surface of the patient;
   extracting a shape feature value for each of a plurality of different body parts of the patient from the deformed generic patient model; and
   estimating a weight for each of the plurality of body parts through respective regression from the shape feature values; and
   dosing the patient with radiation where an amount of radiation is based on a summed weight of the plurality of body parts.

10. The method of claim 9 wherein estimating comprises estimating with a machine-learned regressor.

* * * * *